United States Patent
Yun et al.

(10) Patent No.: US 11,262,347 B2
(45) Date of Patent: Mar. 1, 2022

(54) DEVICE AND METHOD FOR BLOOD PLASMA SEPARATION

(71) Applicant: CURIOSIS Co., Ltd., Seoul (KR)

(72) Inventors: Ho Young Yun, Uijeongbu-si (KR); Sung Young Choi, Yongin-si (KR)

(73) Assignee: CURIOSIS CO., LTD., Seoul (KR)

( * ) Notice: Subject to any disclaimer, the term of this patent is extended or adjusted under 35 U.S.C. 154(b) by 457 days.

(21) Appl. No.: 15/969,850

(22) Filed: May 3, 2018

(65) Prior Publication Data
US 2019/0339253 A1 Nov. 7, 2019

(51) Int. Cl.
G01N 33/49 (2006.01)
B01L 3/00 (2006.01)
A61M 1/34 (2006.01)

(52) U.S. Cl.
CPC ............. G01N 33/491 (2013.01); A61M 1/34 (2013.01); B01L 3/502753 (2013.01); B01L 2200/10 (2013.01); B01L 2300/0819 (2013.01)

(58) Field of Classification Search
CPC ..................... G01N 33/491; B01L 3/502753
See application file for complete search history.

(56) References Cited

U.S. PATENT DOCUMENTS

| | | | | |
|---|---|---|---|---|
| 5,587,128 A * | 12/1996 | Wilding | ............... | B01D 61/18 216/2 |
| 6,555,387 B1 * | 4/2003 | Berndt | ............... | G01N 1/2813 422/401 |
| 2003/0089605 A1 * | 5/2003 | Timperman | ..... | G01N 27/44743 204/450 |
| 2008/0135502 A1 * | 6/2008 | Pyo | ................. | B01D 21/0075 210/801 |
| 2010/0300942 A1 * | 12/2010 | Sulchek | ............ | B07B 13/003 209/132 |

(Continued)

FOREIGN PATENT DOCUMENTS

KR   10-2011-0005963    1/2011
KR      10-1750936     6/2017

OTHER PUBLICATIONS

Choi et al., Continuous blood cell separation by hydrophoretic filtration, Lab Chip, 2007, 7, 1532-1538 (Year: 2007).*

(Continued)

Primary Examiner — Catharine L Anderson
Assistant Examiner — Arjuna P Chatrathi
(74) Attorney, Agent, or Firm — Lex IP Meister, PLLC

(57) ABSTRACT

A chip for blood plasma separation includes: (i) a body part, in which a sealed space through which blood can flow is integrally formed and the channel part and a ridge are alternately and continuously formed; (ii) an inflow part, which is disposed at an upper region of the body part into which the blood inflows; (iii) an outlet for discharging blood cells located at one side surface of the body part; and (iv) an outlet for discharging blood plasma located at the other side surface of the body part, in which the ridge is formed discretely, a chip array for blood plasma separation including the chip for blood plasma separation, a device for blood plasma separation including the chip for blood plasma separation and/or the chip array for blood plasma separation, and a method for blood plasma separation using the device.

18 Claims, 12 Drawing Sheets

(56) References Cited

U.S. PATENT DOCUMENTS

2011/0065181 A1* 3/2011 Hvichia ............... G01N 33/491
                                                              435/325
2014/0174994 A1   6/2014 Bemate
2016/0161378 A1* 6/2016 Kim ..................... G01N 1/4077
                                                              422/527

OTHER PUBLICATIONS

Choi et al., Hydrophoretic high-throughput selection of platelets in physiological shear-stress range, Lab Chip, 2011, 11, 413-418 (Year: 2011).*

S. Choi et al., "Hydrophoretic high-throughput selection of platelets in physiological shear-stress range", Lab on a Chip, vol. 11, 2011, pp. 413-418, The Royal Society of Chemistry.

J.C. Sturm et al., "Ratchets in hydrodynamic flow: more than waterwheels", Interface Focus, 2014, Royal Society Publishing.

* cited by examiner

DEVICE AND METHOD FOR BLOOD PLASMA SEPARATION

TECHNICAL FIELD

The present invention relates to a technique for blood plasma separation from blood, and more specifically, to a chip for blood plasma separation, which includes: (i) a body part, in which a sealed space through which blood can flow is integrally formed and a channel part and a ridge are alternately and continuously formed; (ii) an inflow part, which is disposed at an upper region of the body part into which the blood flows; (iii) an outlet for discharging blood cells located at one side surface of the body part; and (iv) an outlet for discharging blood plasma located at the other side surface of the body part, in which the ridge is formed discretely, a chip array for blood plasma separation including the chip for blood plasma separation, a device for blood plasma separation including the chip for blood plasma separation and/or the chip array for blood plasma separation, and a method for blood plasma separation using the device.

BACKGROUND ART

Blood is largely divided into solid and liquid components, and the solid component includes blood cells such as red blood cells and white blood cells, while the liquid component includes blood plasma. In the present specification, blood plasma is defined as a liquid component that contains blood platelets, and includes about 90 volume % of water, about 7-8 volume % of plasma proteins, and additionally, lipids, saccharides, inorganic salts, and non-protein nitrogen compounds including urea, amino acids, uric acid, etc. The plasma proteins mainly contain albumin and globulin, and also contain fibrinogen that is related to blood coagulation. The lipids may contain cholesterol, lecithin, etc. The inorganic salts may contain sodium, chlorine, potassium, calcium, magnesium, etc., and play an important role in maintaining normal osmotic pressure in the body. Since each component and content of blood plasma can vary according to conditions of a disease, they can be effectively used for the diagnosis of diseases or conditions of diseases. Additionally, blood plasma can be effectively used in the transfusion of blood components that are transfused to patients in need of useful components contained in blood plasma.

Due to this usefulness, technologies for blood plasma separation have been developed. For example, methods for separating blood cells and blood plasma from blood may include a centrifugation method, a method using a capillary phenomenon, a method of applying an electrical pulse in a microfluidic chip at a right angle to the direction in which the blood flows, etc. However, these conventional technologies for blood plasma separation have drawbacks in that they have low spatial utility due to a large space required for plasma separation, low efficiency of blood plasma separation due to slow blood and blood plasma flow during the process of blood plasma separation, low separation accuracy of the separated blood plasma such that it contains more than a reference value of blood cells, etc.

Accordingly, there is a need for the development of a simple and rapid technique that can separate blood plasma from blood with high separation efficiency and accuracy.

DISCLOSURE

Technical Problem

In the present specification, a simpler and more rapid technique for blood plasma separation from blood with higher separation efficiency and/or accuracy is proposed.

Technical Solution

In an embodiment, a chip for blood plasma separation is provided, which includes:

(i) a body part, in which a space through which blood can flow is integrally formed and a channel part and a ridge are alternately and continuously formed;

(ii) an inflow part, which is disposed at an upper region of the body part into which the blood flows;

(iii) an outlet for discharging blood cells located at one side surface of the body part; and (iv) an outlet for discharging blood plasma located at the other side surface of the body part.

The ridge and the channel part may communicate with each other in the sealed space, the ridge may be formed at an oblique angle of more than 0° and less than 90° with one side surface of the body part while forming a ridge space that communicates with the channel part, and the inclined ridge may be formed discretely by at least one structure that cuts off the inner space in an oblique direction.

The one side surface where the outlet for discharging blood cells is located may be a side surface having an angle of less than 90° with the inclined surface of the ridge, a lower surface connected with the side surface, or an edge region where the side surface is connected with the lower surface, and the other side surface where the outlet for discharging blood plasma is located may be the side opposite to the one side surface where the outlet for discharging blood cells is located, a lower surface connected with the side surface, or an edge region where the side surface is connected with the lower surface.

In another embodiment, a chip array for blood plasma separation is provided, which includes:

(1) a blood inlet into which blood is infused;

(2) a first part for blood plasma separation connected with the blood inlet (1);

(3) a second part for blood plasma separation connected with the first part for blood plasma separation; and (4) a part for discharging blood plasma, in which the first part for blood plasma separation includes at least one chip for blood plasma separation containing a continuous ridge, and the second part for blood plasma separation includes at least one chip for blood plasma separation containing a discrete ridge.

In still another embodiment, a device for blood plasma separation which includes the chip for blood plasma separation or the chip array for blood plasma separation is provided.

The device for blood plasma separation may include at least two chips or chip arrays for blood plasma separation.

The chip for blood plasma separation, the chip array for blood plasma separation, and/or the device for blood plasma separation can separate blood plasma even from a high concentration blood sample from whole blood or blood prepared by 1- to 20-fold dilution of whole blood, with high efficiency and/or accuracy.

In still another embodiment, a method for blood plasma separation using the chip for blood plasma separation, the chip array for blood plasma separation, or the device for blood plasma separation is provided.

DESCRIPTION OF THE DRAWINGS

FIGS. 4 and 5 show test results of a channel clogging phenomenon, in which FIG. 4 shows images illustrating the results of fluorescence staining of blood clots in a device for blood plasma separation including the chip arrays of types 1-3, and in the case of having discrete ridges, there is a high thrombosis rate in proportion to time as compared to the case of having continuous ridges (scale bars: 200 μm).

FIG. 5 is a graph illustrating the results of fluorescence staining (fluorescence intensity) of thrombi obtained in FIG. 4 by digitizing according to time (flow rate of blood infusion: 100 μL/min).

MODE FOR INVENTION

In the present specification, a chip for simpler and more rapid blood plasma separation from blood with higher separation efficiency and/or accuracy, a chip array for blood plasma separation including the chip for blood plasma separation, a device including the chip for blood plasma separation and/or the chip array for blood plasma separation, and a method for blood plasma separation using the chip for blood plasma separation, the chip array for blood plasma separation, and/or the device for blood plasma separation, are proposed.

In an embodiment, a chip for blood plasma separation is provided, which includes:

(i) a body part, in which a sealed space through which blood can flow is integrally formed and the channel part and a ridge are alternately and continuously formed;

(ii) an inflow part, which is disposed at an upper region of the body part into which the blood flows;

(iii) an outlet for discharging blood cells located at one side surface of the body part; and (iv) an outlet for discharging blood plasma located at the other side surface of the body part.

Figure 11:
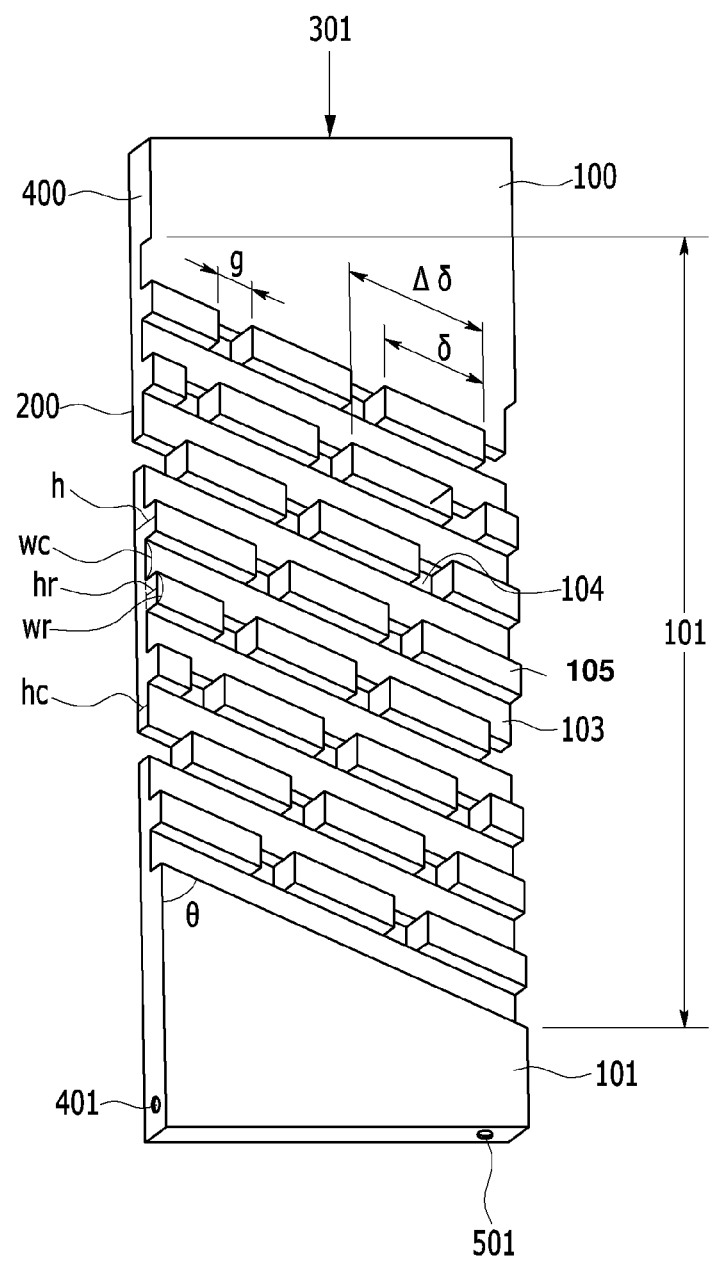
FIG. 11 is a schematic view illustrating an exemplary chip for blood plasma separation having a continuous ridge body (a slant structure).
Figure 12:
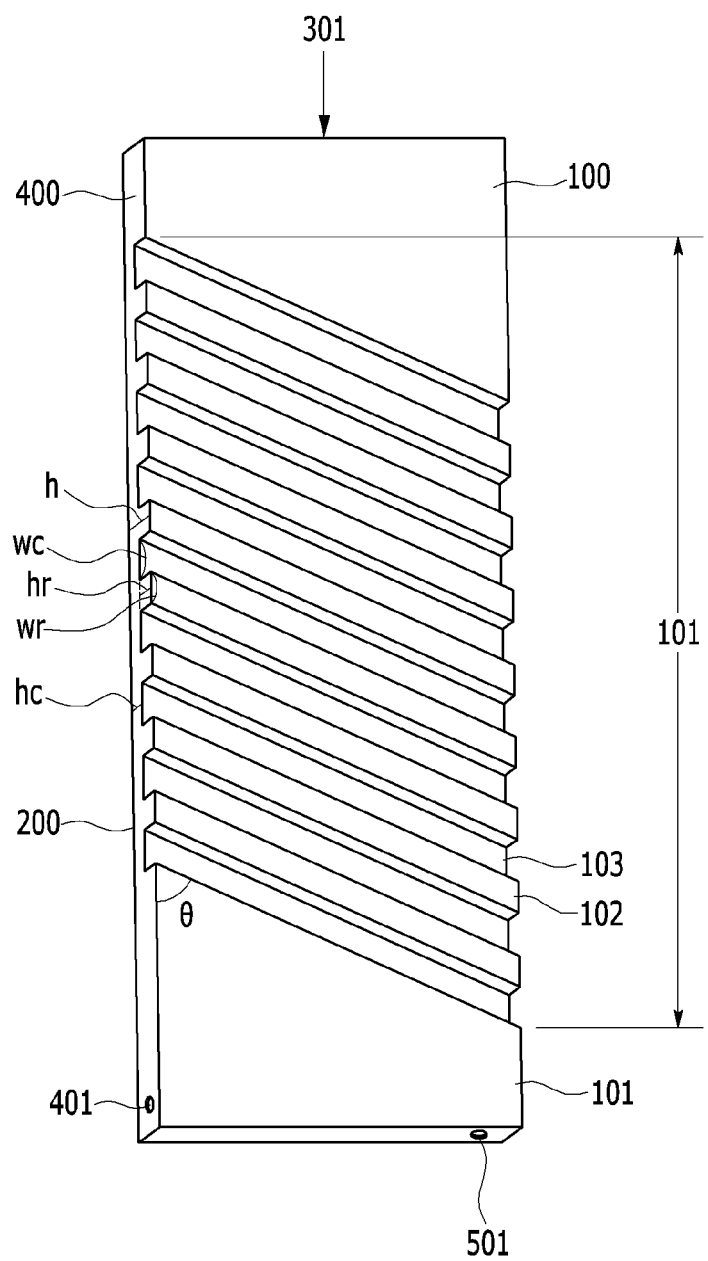
FIG. 12 is a schematic view illustrating an exemplary chip for blood plasma separation having a discrete ridge body (a slant structure).

Illustrative forms of the chip for blood plasma separation provided in the present specification are shown in FIGS. 11 and 12. Hereinafter, explanations are provided with reference to FIGS. 11 and 12. However, the structures of protrusions and depressions shown on the outside of FIGS. 11 and 12 are intended to represent the inner space of the chip, and in fact, these structures of protrusions and depressions are equally formed outside the chip or the device containing the chip, or they may be covered with the outer wall of the chip or device and thus appear to be seen flat from the outside.

A space in which blood can flow in a body part 101 is an inflow part 301 (the upstream region: may be formed as a separate space or may be the upper surface of the body part; the arrow indicates the inflow direction of main blood) that may be a sealed space in a region excluding an outlet for discharging blood cells 401 and an outlet for discharging blood plasma 501, and may be integrally formed so that the blood inflowed from the inflow part can flow to the outlet for discharging blood cells and the outlet for discharging blood plasma.

Ridges 102 (in a continuous state) and 105 (in a discrete state) refer to an inner space in which a groove is formed on one surface of the body part in which the blood flows and thus a space of as much as the groove is further added to the channel part (the groove may appear to be protruded from the chip or outside of the device, or may be covered with an outer wall of the device and thus appear to be flat), while a channel part 103 refers to a region between ridges, and at least one ridge and at least one channel part are alternately and continuously formed in the flow direction of the blood.

The ridges and channel parts communicate with each other in a space where the blood can flow. That is, it is a structure where the blood can flow through the ridge and the channel part that are formed alternately.

The ridge is a region which further includes a space (a ridge space) of as much as the groove, which is formed on one surface in addition to the channel part in the inner space of the body part. The ridge has an inner space having a height (depth: h) of a sum of the height of the channel part (depth: $h_c$) and the height of the ridge space (depth: $h_r$).

The ridge is formed at an oblique angle (θ) of more than 0° and less than 90° with one side surface 400 of the body part (an angle that is formed between one side surface and the ridge toward the direction of blood flow).

The oblique angle of the ridge may be more than 0° and less than 90°, 10° or more and less than 90°, 20° or more and less than 90°, 30° or more and less than 90°, 40° or more and less than 90°, 45° or more and less than 90°, 50° or more and less than 90°, 55° or more and less than 90°, 60° or more and less than 90°, 65° or more and less than 90°, 70° or more and 90° or less, 75° or more and 90° or less, 80° or more and less than 90°, 85° or more and less than 90°, more than 0° and 85° or less, 10° to 85°, 20° to 85°, 30° to 85°, 40° to 85°, 45° to 85°, 50° to 85°, 55° to 85°, 60° to 85°, 65° to 85°, 70° to 85°, 75° to 85°, 80° to 85°, more than 0° and 80° or less, 10° to 80°, 20° to 80°, 30° to 80°, 40° to 80°, 45° to 80°, 50° to 80°, 55° to 80°, 60° to 80°, 65° to 80°, 70° to 80°, 75° to 80°, more than 0° and 75° or less, 10° to 75°, 20° to 75°, 30° to 75°, 40° to 75°, 45° to 75°, 50° to 75°, 55° to 75°, 60° to 75°, 65° to 75°, 70° to 75°, more than 0° and 70° or less, 10° to 70°, 20° to 70°, 30° to 70°, 40° to 70°, 45° to 70°, 50° to 70°, 55° to 70°, 60° to 70°, 65° to 70°, more than 0° and 65° or less, 10° to 65°, 20° to 65°, 30° to 65°, 40° to 65°, 45° to 65°, 50° to 65°, 55° to 65°, 60° to 65°, more than 0° and 60° or less, 10° to 60°, 20° to 60°, 30° to 60°, 40° to 60°, 45° to 60°, 50° to 60°, 55° to 60°, more than 0° and 55° or less, 10° to 55°, 20° to 55°, 30° to 55°, 40° to 55°, 45° to 55°, 50° to 55°, more than 0° and 50° or less, 10° to 50°, 20° to 50°, 30° to 50°, 40° to 50°, or 45° to 50°, with reference to the angle (θ) formed between one side surface and the ridge (one surface of the long axis direction of the ridge) toward the direction of blood flow.

The obliquely formed ridge may be one where the inner space is cut off toward the slant direction and is thus discretely formed so as to form at least one discrete space 105. The disconnection of the inner space of the ridge may include disposing at least one structure 104, such as a post or partition wall formed in the obliquely formed ridge, so that the inner space can be cut off toward the oblique direction or may be patterned so that the ridge forms at least one discrete (cut-off) space toward the oblique direction without any particular structure. Each ridge may include at least two cut-off spaces or at least one pillar or partition wall structure (as such, at least two cut-off spaces may be formed).

At least one ridge is formed, and ridges may not necessarily be in parallel with each other if the angle condition with the one side surface of the body part is satisfied as described above, and for increasing the efficiency of blood plasma separation, the ridges may be in parallel with each other or form an angle of 0° to 30°, 0° to 25°, 0° to 20°, 0° to 15°, 0° to 10°, 0° to 5°, or 0° to 3°, but the condition is not limited thereto.

Additionally, at least two cut-off spaces formed by the discrete ridge may not necessarily be in parallel with each other if the angle condition with the one side surface of the body part is satisfied as described above, and for increasing the efficiency of blood plasma separation, ridges may be in parallel with each other or form an angle of 0° to 30°, 0° to 25°, 0° to 20°, 0° to 15°, 0° to 10°, 0° to 5°, or 0° to 3°, but the condition is not limited thereto.

As such, in the discrete ridge formed obliquely to be higher (deeper) than the height (depth) of the channel part (as high (deep) as the height (depth) of the ridge space), the movement direction and speed of blood becomes different from those of the channel part, and thus the blood cells are supported by the force of different kind and component (size and direction) from that of the channel part and thus the movement of the blood cells changes and they are gathered toward one direction.

In order to separate blood cell components from the blood in the ridge by the induction of a particular movement of blood cells, the ridge space in the ridge must be a space into which at least the entire red blood cells or part thereof can enter. Additionally, when the ridge space becomes a space to include sufficient white blood cells, the red blood cells are not separated but drift along with the blood plasma and are forced to move. Accordingly, the height of the ridge space (depth ($h_r$): the ridge height excluding the height of the channel part hc in the inner space of the ridge) and the width ($w_r$) may be appropriately adjusted to be suitable for the sizes of white blood cells and red blood cells. Additionally, the depth of two or more ridge spaces formed in one ridge may be the same or different from each other. In an embodiment, the height of the ridge space ($h_r$) may be the same or higher than that of the channel part ($h_c$). For example, considering that red blood cells have an average diameter of about 8-10 μm and a thickness of 2-3 μm, and white blood cells have an average diameter of about 15 μm, the height of the ridge (depth: $h_r$) may be 1 μm to 20 μm, 1 μm to 19 μm, 1 μm to 18 μm, 1 μm to 17 μm, 1 μm to 16 μm, 1 μm to 15 μm, 1 μm to 14 μm, 1 μm to 13 μm, 1 μm to 12 μm, 1 μm to 11 μm, 1 μm to 10 μm, 2 μm to 20 μm, 2 μm to 19 μm, 2 μm to 18 μm, 2 μm to 17 μm, 2 μm to 16 μm, 2 μm to 15 μm, 2 μm to 14 μm, 2 μm to 13 μm, 2 μm to 12 μm, 2 μm to 11 μm, 2 μm to 10 um, 3 μm to 20 μm, 3 μm to 19 μm, 3 μm to 18 μm, 3 μm to 17 μm, 3 μm to 16 μm, 3 μm to 15 μm, 3 μm to 14 μm, 3 μm to 13 μm, 3 μm to 12 μm, 3 μm to 11 μm, 3 μm to 10 μm, 4 μm to 20 μm, 4 μm to 19 μm, 4 μm to 18 μm, 4 μm to 17 μm, 4 μm to 16 μm, 4 μm to 15 μm, 4 μm to 14 μm, 4 μm to 13 μm, 4 μm to 12 μm, 4 μm to 11 μm, 4 μm to 10 μm, 5 μm to 20 μm, 5 μm to 19 μm, 5 μm to 18 μm, 5 μm to 17 μm, 5 μm to 16 μm, 5 μm to 15 μm, 5 μm to 14 μm, 5 μm to 13 μm, 5 μm to 12 μm, 5 μm to 11 μm, 5 μm to 10 μm, 6 μm to 20 μm, 6 μm to 19 μm, 6 μm to 18 μm, 6 μm to 17 μm, 6 μm to 16 μm, 6 μm to 15 μm, 6 μm to 14 μm, 6 μm to 13 μm, 6 μm to 12 μm, 6 μm to 11 μm, 6 μm to 10 μm, 7 μm to 20 μm, 7 μm to 19 μm, 7 μm to 18 μm, 7 μm to 17 μm, 7 μm to 16 μm, 7 μm to 15 μm, 7 μm to 14 μm, 7 μm to 13 μm, 7 μm to 12 μm, 7 μm to 11 μm, 7 μm to 10 μm, 8 μm to 20 μm, 8 μm to 19 μm, 8 μm to 18 μm, 8 μm to 17 μm, 8 μm to 16 μm, 8 μm to 15 μm, 8 μm to 14 μm, 8 μm to 13 μm, 8 μm to 12 μm, 8 μm to 11 μm, 8 μm to 10 μm, 9 μm to 20 μm, 9 μm to 19 μm, 9 μm to 18 μm, 9 μm to 17 μm, 9 μm to 16 μm, 9 μm to 15 μm, 9 μm to 14 μm, 9 μm to 13 μm, 9 μm to 12 μm, 9 μm to 11 μm, or 9 μm to 10 μm.

The width ($w_r$) of the ridge space may be the same or different from the height (depth: $h_r$) of the ridge space, and in an embodiment, the width ($w_r$) may have a value that is the same as or greater than that of the height (depth: $h_r$). Additionally, the width of the at least two ridge spaces formed in one ridge may be the same or different from each other. Additionally, in a case where a plurality of ridges of at least two are formed, the width of each ridge may be the same or different from each other. For example, the width of the ridge space or the ridge may be 0.5 to 3 times, 0.5 to 2.5 times, 0.5 to 2 times, 0.5 to 1.5 times, 0.7 to 3 times, 0.7 to 2.5 times, 0.7 to 2 times, 0.7 to 1.5 times, 1 to 3 times, 1 to 2.5 times, 1 to 2 times, or 1 to 1.5 times the height (depth: $h_r$) of the ridge space, but the width is not limited thereto.

The height ($h_c$) of the channel part is sufficient if the components of blood cells, for example, red blood cells (in a case of white blood cells, the size is greater than that of red blood cells, but they are amorphous and thus cannot be modified by the flow rate of the blood to be suitable to pass through the channel), have an appropriate size to pass through it, and there is no particular limitation thereon. For example, the height of the channel part ($h_c$) may be 2 to 20 µm, 2 to 17 µm, 2 to 15 µm, 2 to 12 µm, 5 to 20 µm, 5 to 17 µm, 5 to 15 µm, 5 to 12 µm, 7 to 20 µm, 7 to 17 µm, 7 to 15 µm, 7 to 12 µm, 10 to 20 µm, 10 to 17 µm, 10 to 15 µm, or 10 to 12 µm, but the height is not limited thereto.

The width of the channel ($w_c$) refers to a gap between adjacent ridges, and the width ($w_c$) of at least one channel part may be the same or different from each other. The width of the channel ($w_c$) is not particularly limited, and may be appropriately selected from the width ($w_r$) range of the ridge space described above, but the width is not limited thereto. Additionally, the length (δ) toward the oblique direction of the ridge space is not particularly limited, but it may be adjusted according to the size of the body part and/or the number of ridge spaces discretely formed in one ridge. In another aspect, the number of the discrete ridge spaces may be adjusted according to the length toward the oblique direction of the ridge space. The length (δ) toward the oblique direction of at least two ridge spaces formed in one ridge may be the same or different from each other. In an embodiment, the length (δ) toward the oblique direction of the ridge space may be 2 times or greater, 2.5 times or greater, 3 times or greater, 3.5 times or greater, 4 times or greater, or 4.5 times or greater, relative to the average diameter of red blood cells, and for example, 2 times to 20 times, 2.5 times to 20 times, 3 times to 20 times, 3.5 times to 20 times, 4 times to 20 times, 4.5 times to 20 times, 2 times to 15 times, 2.5 times to 15 times, 3 times to 15 times, 3.5 times to 15 times, 4 times to 15 times, 4.5 times to 15 times, 2 times to 10 times, 2.5 times to 10 times, 3 times to 10 times, 3.5 times to 10 times, 4 times to 10 times, 4.5 times to 10 times, 2 times to 9 times, 2.5 times to 9 times, 3 times to 9 times, 3.5 times to 9 times, 4 times to 9 times, 4.5 times to 9 times, 2 times to 8 times, 2.5 times to 8 times, 3 times to 8 times, 3.5 times to 8 times, 4 times to 8 times, 4.5 times to 8 times, 2 times to 7 times, 2.5 times to 7 times, 3 times to 7 times, 3.5 times to 7 times, 4 times to 7 times, 4.5 times to 7 times, 2 times to 6 times, 2.5 times to 6 times, 3 times to 6 times, 3.5 times to 6 times, 4 times to 6 times, 4.5 times to 6 times, 2 times to 5 times, 2.5 times to 5 times, 3 times to 5 times, 3.5 times to 5 times, 4 times to 5 times, or 4.5 times to 5 times, relative to the average diameter of red blood cells, but the length (δ) is not limited thereto.

The gap between ridge spaces in one ridge (g; that is, the length of the structure that cuts off the inner space of the ridge (the width of the structure is determined according to the width of the ridge)) suffices if it is the minimum gap or greater that can physically divide the ridge space into two or more. Although there is no particular upper limit, but it may be shorter than the length of the ridge space considering the efficiency of plasma separation. In an embodiment, the gap (g) between the ridge spaces may be 0.01 µm to 100 µm, 0.01 µm to 90 µm, 0.01 µm to 80 µm, 0.01 µm to 70 µm, 0.01 µm to 60 µm, 0.01 µm to 50 µm, 0.01 µm to 45 µm, 0.01 µm to 40 µm, 0.01 µm to 35 µm, 0.01 µm to 30 µm, 0.01 µm to 25 µm, 0.01 µm to 20 µm, 0.01 µm to 15 µm, 0.01 µm to 12 µm, 0.01 µm to 10 µm, 0.1 µm to 100 µm, 0.1 µm to 90 µm, 0.1 µm to 80 µm, 0.1 µm to 70 µm, 0.1 µm to 60 µm, 0.1 µm to 50 µm, 0.1 µm to 45 µm, 0.1 µm to 40 µm, 0.1 µm to 35 µm, 0.1 µm to 30 µm, 0.1 µm to 25 µm, 0.1 µm to 20 µm, 0.1 µm to 15 µm, 0.1 µm to 12 µm, 0.1 µm to 10 µm, 1 µm to 100 µm, 1 µm to 90 µm, 1 µm to 80 µm, 1 µm to 70 µm, 1 µm to 60 µm, 1 µm to 50 µm, 1 µm to 45 µm, 1 µm to 40 µm, 1 µm to 35 µm, 1 µm to 30 µm, 1 µm to 25 µm, 1 µm to 20 µm, 1 µm to 15 µm, 1 µm to 12 µm, or 1 µm to 10 µm, but the gap is not limited thereto.

The inflow part 301 may include an inflow inlet into which blood flows and which supplies the inflowed blood to the body part, or may have an inflow inlet into which blood flows. The inflow inlet may be directly connected with the body part, or may be randomly connected to the body part through a cavity that includes an empty space communicating with the inflow part and the body part. The inflow part of blood may be located at an upper region of the body part, and in particular, the upper region refers to an upstream region where the blood flow begins in the body part.

The one side surface where the outlet for discharging blood cells 401 is located may refer to a side surface of the body part having an angle of greater than 0° and less than 90° with the ridge (an angle formed between the ridge and the one side surface 400 toward the direction of blood movement), a lower surface connected with the side surface 400, or an edge region where the side surface 400 is connected with the lower surface. Additionally, the other side surface where the outlet for discharging blood plasma 501 is located is the side opposite to the one side surface where the outlet for discharging blood cells is located, a lower surface connected with the side surface, or an edge region where the side surface is connected with the lower surface.

The outlet for discharging blood cells and the outlet for discharging blood plasma may be directly connected with the body part, or may be randomly connected to the body part through a cavity that includes an empty space communicating with the outlet and the body part.

The side surface refers to surfaces on both sides with reference to the direction of blood movement in the body part. FIG. 11 and FIG. 12 provide embodiments where one side surface, which forms an angle of greater than 0° and less than 90° with the inclined ridge (a slant structure), is on the right with reference to the direction of blood movement, however, when the one side surface is on the opposite direction with reference to the direction of blood movement (i.e., when it is on the left with reference to the direction of blood movement), the ridge may have a slant structure so that the angle formed with the side surface on the left toward the direction of blood movement can be an oblique angle of greater than 0° and less than 90°.

In an embodiment, the chip for blood plasma separation may be manufactured by attaching (fixing) the surface where the protrusions and depressions of the body part (including the ridge (a continuous structure: 102; a discrete structure: 105), the channel part 103, and the structure 104 that randomly cuts off the inner space of the ridge) are formed, and both side surfaces of a structure 100 which includes both side surfaces or the structure 104 that cuts off both side surfaces and the inner space of the ridge.

In particular, the structure 100 and a substrate 200 may be manufactured using a solid material which is the same or different from each other, but the specific material is not particularly limited. The structure 100 and the substrate 200 may be manufactured using a material selected from the group consisting of, for example, commonly used polymers such as polystyrene (PS), polycarbonate (PC), polymethylmethacrylate (PMMA), polyethylene terephthalate (PET), and polydimethylsiloxane (PDMS); photoresist materials such as SU-8, polyethylene glycol diacrylate (PEG-DA), etc.; metals such as aluminum, iron, platinum, copper, etc.; a soft solid such as silicone, etc.; glass, etc., but the materials for manufacturing the structure 100 and the substrate 200 are not limited thereto.

The size of the chip for blood plasma separation is not particularly limited, and for example, the vertical size (the direction of blood movement) may be about 1 mm to about 100 mm, about 1 mm to about 50 mm, about 1 mm to about 30 mm, about 1 mm to about 20 mm, or about 1 mm to about 10 mm, and the horizontal size may be about 100 μm to about 2000 μm, about 100 μm to about 1800 μm, about 100 μm to about 1500 μm, about 100 μm to about 1300 μm, about 100 μm to about 1000 μm, about 300 μm to about 2000 μm, about 300 μm to about 1800 μm, about 300 μm to about 1500 μm, about 300 μm to about 1300 μm, or about 300 μm to about 1000 μm, but the sizes are not limited thereto.

In another embodiment, a chip array for blood plasma separation including at least two chips for blood plasma separation is provided. The at least two chips for blood plasma separation may be, for example, those in which 2 to 10, 2 to 7, 2 to 5, 2 to 4, 2 or 3, 3 to 10, 3 to 7, 3 to 5, or 3 or 4 chips for blood plasma separation are coupled in series. At least one among the at least two chips for blood plasma separation may be a chip for blood plasma separation having a discrete ridge (see FIG. 12). In still another embodiment, the chip array for blood plasma separation may be one which further includes at least one chip for blood plasma separation having a continuous ridge (FIG. 11), for example, in the upstream direction of the chip for blood plasma separation having the discrete ridge (the direction having a blood inlet), in addition to the chip for blood plasma separation having the discrete ridge (FIG. 12). As such, by including the continuous ridge to a region adjacent to the blood inlet, blood coagulation and channel clogging that may occur in the chip for blood plasma separation having the discrete ridge during the blood flow can be prevented.

In an embodiment, the chip array for blood plasma separation may include at least one chip for blood plasma separation including a continuous ridge, which includes:

(1) a blood inlet into which blood is infused;

(2) a first part for blood plasma separation connected with the blood inlet (1);

(3) a second part for blood plasma separation connected with the first part for blood plasma separation; and (4) a part for discharging blood plasma, wherein the first part for blood plasma separation is connected so that the blood infused into the blood inlet inflows, and includes at least one chip for blood plasma separation including a continuous ridge, including:

(i-1) a body part, in which a space through which blood can flow is integrally formed and the (at least one) channel part and the (at least one) ridge are alternately and continuously formed, (ii-1) an inflow part, which is formed at an upper region of the body part into which the blood flows, (iii-1) an outlet for discharging blood cells formed at one side surface of the body part; and (iv-1) an outlet for discharging blood plasma formed at the other side surface of the body part, wherein the ridge and the channel part communicate with each other in the sealed space, the ridge is formed at an oblique angle of more than 0° and less than 90° with one side surface of the body part while forming a ridge space that communicates with the channel part, the inclined ridge is formed continuously in an oblique direction (i.e., there is no cut-off of the ridge space), the one side surface where the outlet for discharging blood cells is located is a side surface having an angle of greater than 0° and less than 90° (the angle formed between the ridge and one side surface toward the direction of blood movement) with the inclined surface of the ridge, a lower surface connected with the side surface, or an edge region where the side surface is connected with the lower surface, and the other side surface where the outlet for discharging blood plasma is located is the side opposite to the one side surface where the outlet for discharging blood cells is located, a lower surface connected with the side surface, or an edge region where the side surface is connected with the lower surface.

The second part for blood plasma separation is connected so that the blood plasma discharged from the part for discharging blood plasma of the ridge included in the first part for blood plasma separation inflows, and includes at least one fluidic chip for blood plasma separation including the discontinuous ridge as described above.

In an embodiment, the first part for blood plasma separation includes at least one fluidic chip for blood plasma separation including the continuous ridge, and the second part for blood plasma separation includes at least two chips (e.g., two chips) for blood plasma separation including the discontinuous ridges.

In another embodiment, a device for blood plasma separation including at least one (e.g., at least two, at least four, at least six, or at least eight) chip array for blood plasma separation is provided. There is no upper limit with regard to the number of chip arrays included in the device for blood plasma separation, and the chip arrays may be included at a number allowed by the spatial conditions of the device for blood plasma separation. For example, the number of chip arrays included in the device for blood plasma separation may be 1 to 100, 1 to 80, 1 to 60, 1 to 50, 1 to 40, 1 to 30, 1 to 20, 1 to 10, 2 to 100, 2 to 80, 2 to 60, 2 to 50, 2 to 40, 2 to 30, 2 to 20, or 2 to 10, but the number of chip arrays is not limited thereto. The amount of blood that can be treated by one device for blood plasma separation increases in proportion to the number of the chip arrays for blood plasma separation included in the device for blood plasma separation.

In an embodiment, being included in each chip array for blood plasma separation, the first part for blood plasma separation may include at least one chip (e.g., 1 to 10, 1 to 5, 1 to 3, or 1) for blood plasma separation including the continuous ridge, and the second part for blood plasma separation may include at least two chips (e.g., at least 1 or at least 2, e.g., 1 to 30, 1 to 25, 1 to 20, 1 to 15, 1 to 10, 1 to 8, 1 to 5, 1 to 3, 2 to 30, 2 to 25, 2 to 20, 2 to 15, 2 to 10, 2 to 8, 2 to 5, 2 to 3, or 2) for blood plasma separation including the discontinuous ridges. The at least two chip arrays included in each device for blood plasma separation may be connected in parallel.

In still another embodiment, the device for blood plasma separation may further include a blood cell reservoir for storing blood cells discharged from the at least two chip arrays for blood plasma separation. The stored and/or separated blood cells may be recycled for a desired use. Additionally, the device for blood plasma separation may further include a blood plasma reservoir for storing blood plasma discharged from the at least two chip arrays for blood plasma separation.

The chip for blood plasma separation, the chip array for blood plasma separation, and/or the device for blood plasma separation may be used to induce a blood flow from the inlet to the opposite side at the blood infusion speed. The rate of blood infusion suffices as long as it is at least a rate that can induce blood flow. For example, the blood infusion speed for each chip array for blood plasma separation may be at least about 10 µL/min, about 20 µL/min, about 30 µL/min, about 40 µL/min, about 50 µL/min, about 60 µL/min, about 70 µL/min, or about 80 µL/min, and its upper limit may be about 1000 µL/min, about 900 µL/min, about 800 µL/min, about 700 µL/min, about 600 µL/min, about 500 µL/min, about 450 µL/min, about 400 µL/min, about 350 µL/min, about 300 µL/min, about 250 µL/min, about 200 µL/min, about 150 µL/min, or about 120 µL/min, but the blood infusion speed is not limited thereto. The blood infusion speed of the device for blood plasma separation may be set to increase in proportion to the blood infusion speed of the chip array for blood plasma separation according to the number of chip arrays included in the device.

In an embodiment, the chip for blood plasma separation, the chip array for blood plasma separation, and/or the device for blood plasma separation may be used by being connected with a supplier part that can supply and/or infuse blood to a blood inflow part or blood inlet.

Figure 10:
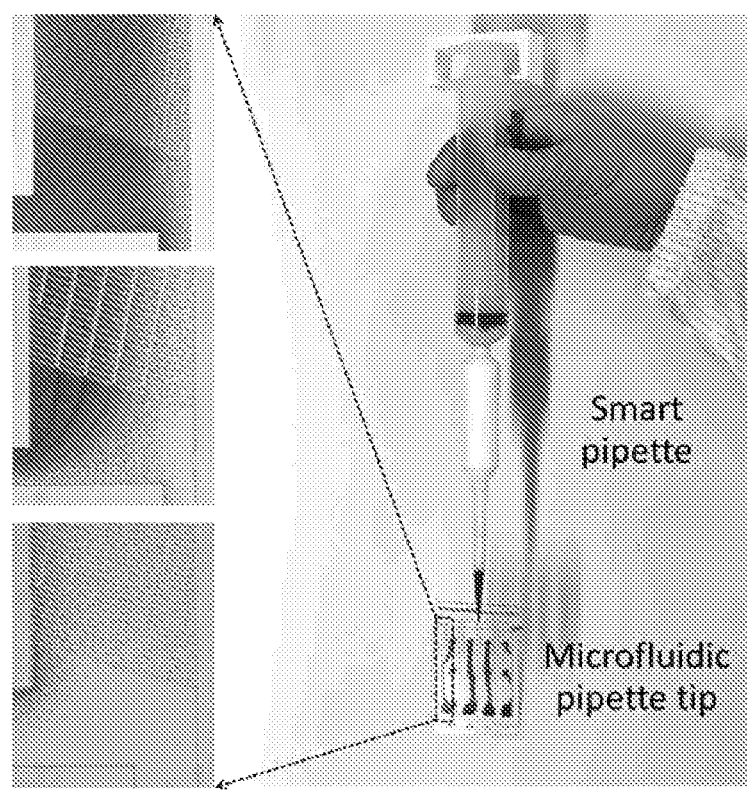
FIG. 10 shows an embodiment where a device for blood plasma separation is applied to a pipette.

In another embodiment, a kit for blood plasma separation is provided, which includes a chip for blood plasma separation, a chip array for blood plasma separation, and/or a device for blood plasma separation, and a blood supply part, which is connected with a blood inlet or blood inflow part of the chip for blood plasma separation, the chip array for blood plasma separation, and/or the device for blood plasma separation. The blood supply part may be configured to control the blood infusion rate by storing the blood and/or compressing it, and for example, it may be at least one selected from the group consisting of a syringe, a pipette, and a pump such as a piston pump, a syringe pump, a diaphragm pump, a peristaltic pump, etc. In an embodiment, the blood supply part may be used in a form where the blood inlet of the device for blood plasma separation is connected with a needle of a syringe (see FIG. 10).

In another embodiment, a method for blood plasma separation using a chip for blood plasma separation, a chip array for blood plasma separation, and/or a device for blood plasma separation is provided.

Specifically, the method for blood plasma separation includes:

infusing blood into the chip for blood plasma separation, the chip array for blood plasma separation, and/or the device for blood plasma separation; and collecting the blood plasma being discharged from the chip for blood plasma separation, the chip array for blood plasma separation, and/or the device for blood plasma separation.

The method for blood plasma separation has an advantage in that blood plasma can be separated with high efficiency from whole blood or even blood in a state of having a relatively high concentration of blood cells. In an embodiment, the blood to be infused may be whole blood, or blood prepared by a 1- to 20-fold dilution of the whole blood based on volume, but the blood is not limited thereto.

By the method of blood plasma separation, the purity of the separated blood plasma (i.e., separation purity: the number of red blood cells discharged/the number of red blood cells infused) may be about at least 90%, about at least 93%, about at least 94%, about at least 95%, about at least 95.5%, about at least 96%, about at least 96.5%, about at least 97%, about at least 97.5%, about at least 98%, about at least 98.5%, about at least 99%, or about at least 99.5%. The purity of the separated blood plasma may be related to the amount of blood infusion (e.g., the smaller the amount of blood infusion, the higher the purity of the separated blood plasma), and for further increasing the efficiency of blood plasma separation, the amount of blood infusion (i.e., blood infusion speed) to be applied to one chip array for blood separation may be adjusted in the range of about 10 µL/min to about 1000 µL/min, about 10 µL/min to about 900 µL/min, about 10 µL/min to about 800 µL/min, about 10 µL/min to about 700 µL/min, about 10 µL/min to about 600 µL/min, about 10 µL/min to about 500 µL/min, about 10 µL/min to about 400 µL/min, about 10 µL/min to about 350 µL/min, about 10 µL/min to about 300 µL/min, about 10 µL/min to about 250 µL/min, about 10 µL/min to about 200 µL/min, about 10 µL/min to about 150 µL/min, about 50 µL/min to about 1,000 µL/min, about 50 µL/min to about 900 µL/min, about 50 µL/min to about 800 ul/min, about 50 µL/min to about 700 µL/min, about 50 µL/min to about 600 µL/min, about 50 µL/min to about 500 µL/min, about 50 µL/min to about 400 µL/min, about 50 µL/min to about 350 µL/min, about 50 µL/min to about 300 µL/min, about 50 µL/min to about 250 µL/min, about 50 µL/min to about 200 µL/min, or about 50 µL/min to about 150 µL/min.

Additionally, by the method for blood plasma separation, the recovery rate of blood plasma (i.e., the volume of collected blood plasma/the volume of infused blood plasma) may be in the range of about 5% to about 15%.

The chip for blood separation, the chip array for blood separation, and/or the device for blood separation provided in the present specification and the method of using the same may be able to separate blood plasma in a simpler and more rapid manner.

Examples

Hereinafter, for explanation of the present invention, the advantages in implementation of the present invention, and the objects achieved by the implementation of the present invention, preferred exemplary embodiments of the present invention will be illustrated and described with reference to these embodiments. First, the terms used in the present application are used only to describe specific exemplary embodiments and are not intended to limit the scope of the present invention, and singular expressions may include plural expressions, unless otherwise explicitly indicated by the context. Additionally, in the present specification, the terms "comprise (include)" or "have" are intended to specify that there are features, numbers, steps, actions, constituent elements, parts, or combinations thereof described in the specification, and they do not exclude the presence or addition of one or more other features, numbers, steps, actions, constituent elements, parts, or combinations thereof. Additionally, in the present specification, the numerical range expressed as "A to B" means all numbers (real numbers) between A and B, including A and B, and may also be interpreted to include the values of an approximation of A and B which are recognized as equal ranges.

Hereinafter, the present invention will be described in more detail through exemplary embodiments. These exemplary embodiments are only to explain the present invention more specifically, and it will be apparent to those of ordinary skill in the art to which the present invention belongs that the range of the present invention is not limited by these exemplary embodiments.

Example 1: Design and Manufacture of Microfluidic Chip for Blood Plasma Separation Chips of polydimethylsiloxane (PDMS, Dow Corning, USA) for blood plasma separation were manufactured. The master mold for manufacturing the PDMS chip was manufactured using photolithography. Since this chip has a two-step height, the chips were manufactured by twice repeating a process of coating of a photoresist (SU-8, Microchem, USA), mask alignment, exposure to ultraviolet rays, and development on a silicon wafer. The manufactured master mold was treated with silane (trichlorosilane, Sigma Aldrich, USA) to facilitate the release of PDMS. PDMS in which a base and a curing agent were mixed at a 10:1 ratio was poured into the silane-treated master mold, bubbles therein were removed, and the mixture was cured by heating. The fully-cured PDMS was removed from the master mold and holes were punched through the inlet and the outlet, followed by bonding with glass through oxygen plasma treatment. The height of the channel part of the chip ($h_c$) was set to 12 μm, the width ($w_r$) of a continuous slant array (CSA) was set to 15 μm, and the height of the continuous slant array (CSA) was set to 15 μm. In the case of a discrete slant array (DSA), the height of the channel part of the chip ($h_c$) was set to 12 μm, the width ($w_r$) was set to 15 μm, the size of microposts was set to 30 μm, and the slant direction length (d) of each cut-off slant structure was set to 160 μm. The width of each CSA or DSA was set to 1 cm and their length was set to 1.7 cm (when three are connected in parallel, the total length becomes about 5 cm). The discrete array (DSA), which is interrupted due to the microposts, can minimize the dispersion of red blood cells as shown in the lower part of FIG. 1, and thus can bring an advantageous effect of obtaining pure blood plasma. For hand held operation of a microfluidic chip, a 1 mL pipette tip was inserted into a 60 mL syringe.

Example 2: Test of Blood Plasma Separation Using Microfluidic Chip for Blood Plasma Separation Sample Preparation The blood of dogs and humans used in the experiment was purchased from Korea Animal Blood Bank and Korea Red Cross, and the red blood cell volume rate (hematocrit) was measured by measuring the length of red blood cells which were concentrated by centrifugation after loading the blood in a capillary tube. In the case of blood clots, the analysis was performed using SYTO 13 (Thermo Fisher Scientific, USA), which is a fluorescent material capable of staining nuclei of white blood cells in blood clots. The efficiency of blood plasma separation was measured using the hematocytometer (Invitrogen, USA).

Experimental Conditions

The efficiency of blood plasma separation of chips according to the conditions of the amount of flow (100 μL/min to 400 μL/min) was measured using a syringe pump (KD Scientific, USA), and once the optimum amount of flow was determined, the experiment was performed using 1 ml pipettes that can maintain the amount of flow at a constant level. The movement of blood cells within a chip was observed using a microscope (Nikon, Japan) by installing a CCD camera (Nikon, Japan) and a high speed camera (Vision Research, USA) thereon. The fluorescent images were analyzed using the ImageJ (National Institutes of Health, USA), which is software for image analysis.

Results

The flow of a liquid within an inclined structure for the separation of blood cells proceeds in the direction parallel with the inclined structure, and a flow of the liquid in the opposite direction (i.e., a direction where blood cells are gathered) occurs in the lower part of the inclined structure. In particular, when the cell size is sufficiently large (d≥h/2, where d is the cell diameter), there is a force applied toward the lower part of the inclined structure which affects the flow of the liquid in the lower part of the inclined structure and thereby the cells move in a direction vertical to the inclined structure (i.e., a direction where blood cells are gathered). Since the number of red blood cells in blood is inevitably high, there are cells that are essentially present which are forced toward the inclined structure (leading to undesired deviation along the deviation path) and the purity of the blood plasma recovered in the final stage is lowered. To increase the efficiency of blood cell separation and improve the amount and purity of blood plasma being recovered by minimizing such a phenomenon, a discrete inclined structure was developed. The discrete slant array (DSA) has an inclined structure of 160 μm in length and the inclined structure is separated by a micropost of a 30 μm width (104 of FIG. 12). Each inclined structure of the DSA was manufactured by moving from the inclined structure immediately ahead thereof by Δδ (see the right image of FIG. 1). The inclined structure moved by Δδ plays a role of maintaining the movement of blood cells toward the focusing path (a direction that blood cells are gathered, a vertical direction of the inclined structure). The microposts between the inclined structures are forced to move upward along the focusing path by the blood cells being gathered and thereby aid the blood cells which move toward the opposite direction to again move downward along the focusing path. The DSA performing such a function can maximize the purity of the separated blood plasma.

Figure 1:
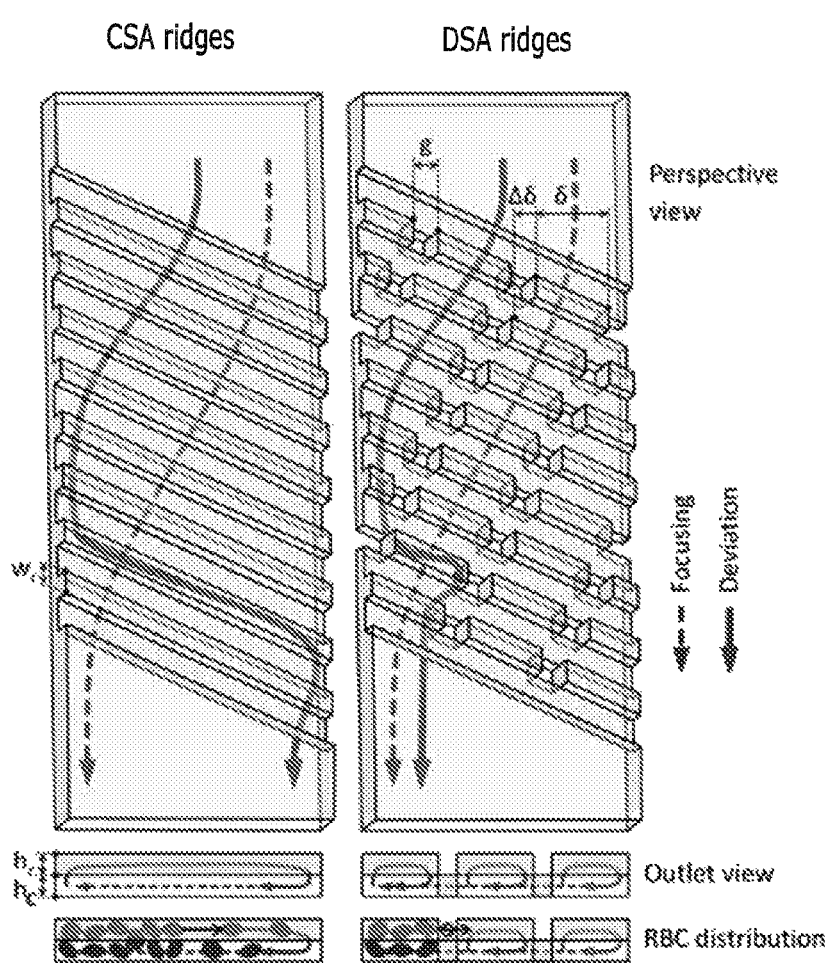
FIG. 1 is a schematic representation of a chip for blood separation according to an exemplary embodiment, in which the left side of the upper part shows the structure of the chip with continuous slant array (CSA) ridges and the movement of blood cells; the right side of the upper part shows the structure of the chip with discrete slant array (DSA) ridges formed by micro-posts and the movement of blood cells; the left side of the lower part shows the movement of blood cells in the chip section including the CSA ridges; and the right side of the lower part shows the movement of blood cells in the chip section including the DSA ridge ($W_r$: width of ridge space; $h_r$: height of ridge space; h: height of channel; g: gap of ridge space; δ: length of ridge space; Δδ: gap between ridges; dotted line arrow: focused pathway of movement of blood cells; and solid line arrow: pathway of movement of deviated blood cells).
Figure 2:
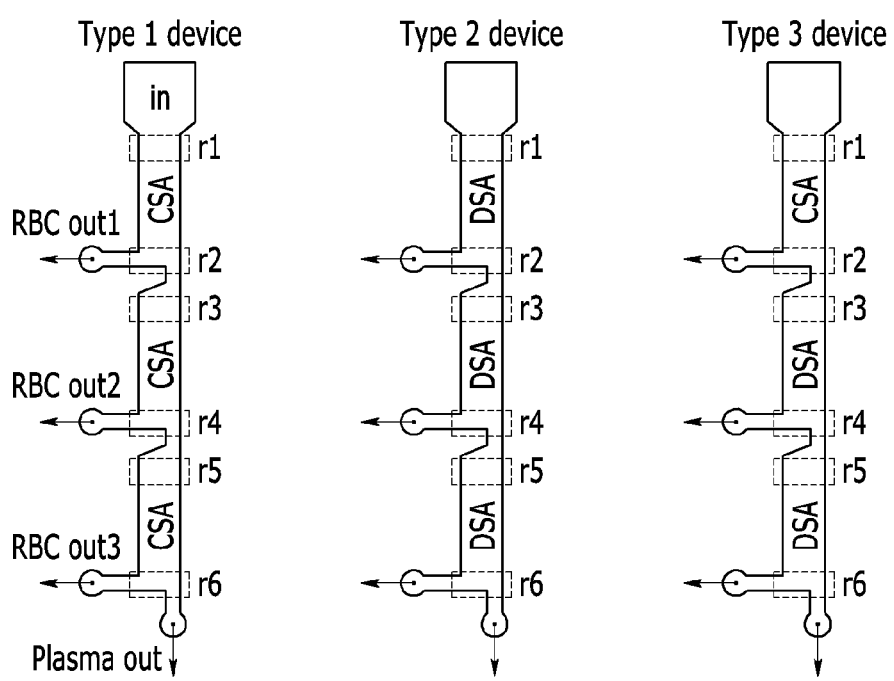
FIG. 2 is a schematic representation of three different types of chip arrays for blood plasma separation, in which type 1 shows a shape of a chip array where three chips having a CSA ridge (the first chip to the third chip) are coupled in parallel; type 2 shows a shape of a chip array where three chips having a DSA ridge (the first chip to the third chip) are coupled in parallel; and type 3 shows a shape of a chip array where one chip having a CSA ridge (the first chip) and two chips having a DSA ridge (the second chip and the third chip) are sequentially coupled in parallel (each of r1 to r6 represents the segment of the indicated position).
Figure 3:
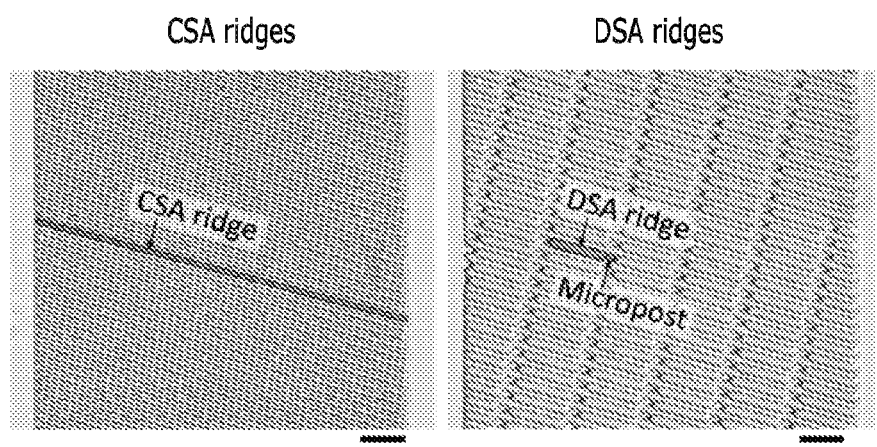
FIG. 3 shows bright-field micrographs illustrating CSA ridges and DSA ridges (scale bars: 100 μm).

FIG. 1 schematically shows the process of blood plasma separation in the chips for blood plasma separation having a continuous inclined structure (slant array ridges) (the image on the left) and in the chips for blood plasma separation having a discrete (separated) inclined structure (slant array ridges) (the image on the right). The discrete inclined structure enables prevention of the deviation, which is a phenomenon in which blood cells can move along the inclined structure by the microposts between the inclined structures toward the opposite direction, and thereby prevents the dispersion of blood cells and maximizes the efficiency of separation. FIG. 2 schematically shows three different types of chip arrays for blood plasma separation prepared by combination of CSA and DSA (type 1: consisting of three CSAs; type 2: three DSAs; and type 3: one CSA and two DSAs). FIG. 3 shows microscope images of CSA and DSA.

Figure 4:
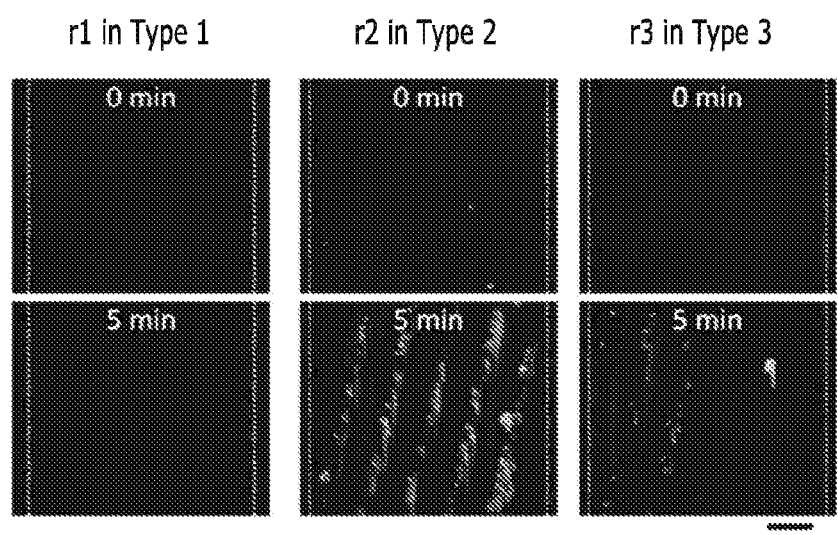
Figure 5:
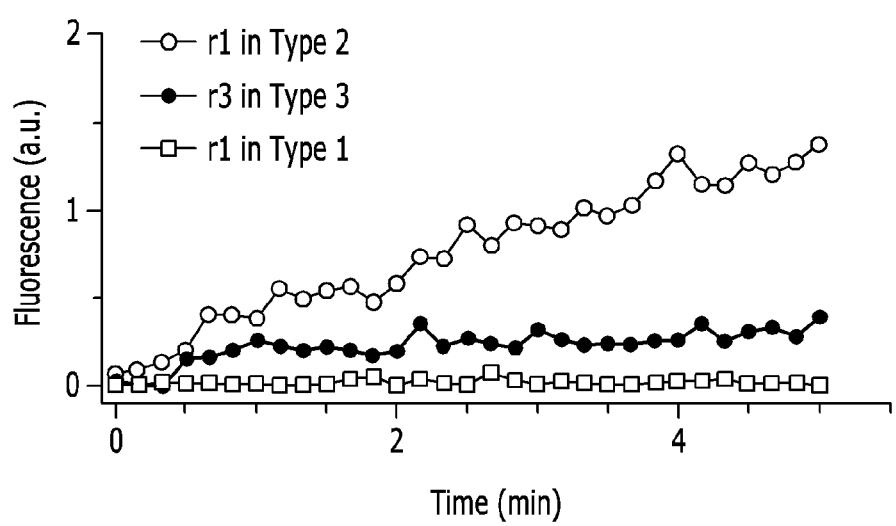

The channel clogging phenomenon in the case where blood is separated was tested using the three kinds of chip arrays for blood plasma separation exemplified in FIG. 2. The channel clogging phenomenon was evaluated by fluorescent staining of blood clots. The amount of blood infusion was tested based on 100 μL/min. The obtained results are shown in FIGS. 4 and 5. FIG. 4 shows the obtained fluorescent images, and it was confirmed that in the case of the chip array of type 2, the channel clogging phenomenon was distinctive due to the clogging of blood clots in the microposts and that such a phenomenon of clogging was worsened with time (as more blood flowed). The changes in the intensity of the obtained fluorescence are shown as a graph in FIG. 5. It was confirmed in FIG. 5, the same as in FIG. 4, that the clogging was worsened with time in the case of the chip array of type 2 which includes only DSAs.

As can be seen in FIGS. 4 and 5, although DSA has higher efficiency of blood plasma separation compared to CSA, CSA causes no channel clogging phenomenon because blot clots are not clogged, whereas DSA causes the channel clogging phenomenon because microposts are disposed at about 100 μm intervals and thus blood clots are clogged. Therefore, for the separation of blood plasma with high efficiency without any channel clogging phenomenon, it may be advantageous to manufacture the chip array to have at least two regions (e.g., three regions) where at least the first region (chip) is manufactured to include a CSA while the remaining regions are manufactured to include a DSA.

Figure 6:
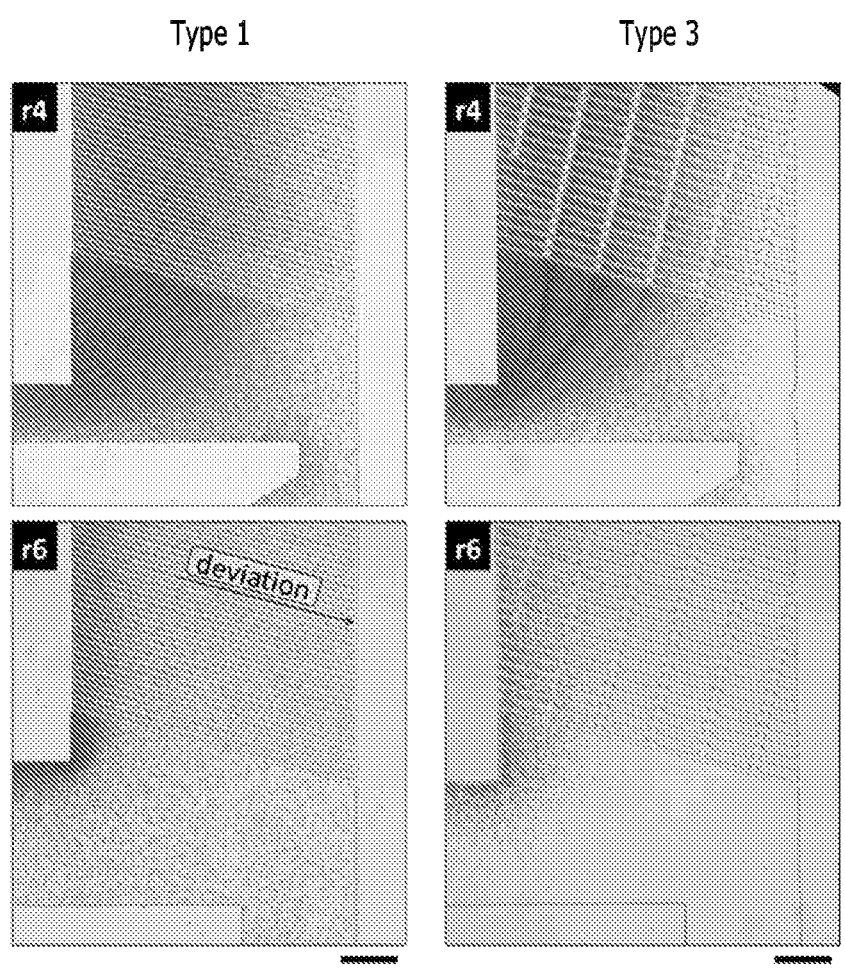
FIG. 6 shows images illustrating undesired deviation of RBCs departed from a focused RBC stream in type 1 and type 3 arrays for blood plasma separation, and it can be confirmed that the undesired deviation of RBCs can be perfectly embodied in the type 3 device for blood plasma separation (in each image, the blood flow direction is in the direction from an upper region to a lower part, and the infusion flow rate is set to 100 μL/min; scale bars: 200 μm).

FIG. 6 shows comparison results of efficiencies of blood plasma separation between chip arrays of type 1 and type 3, in which the chip array of type 1 where all the regions consist of CSAs shows low efficiency of blood plasma separation because there is a high amount of blood cells that move along the inclined structure toward the opposite direction, whereas the chip array of type 3 where only the first region consists of a CSA and the remaining two channels consist of DSAs does not have blood cells that move along the inclined structure toward the opposite direction, thus providing excellent purity of blood plasma in the final recovery part. The amount of blood flow was tested based on 100 μL/min.

Figure 7:
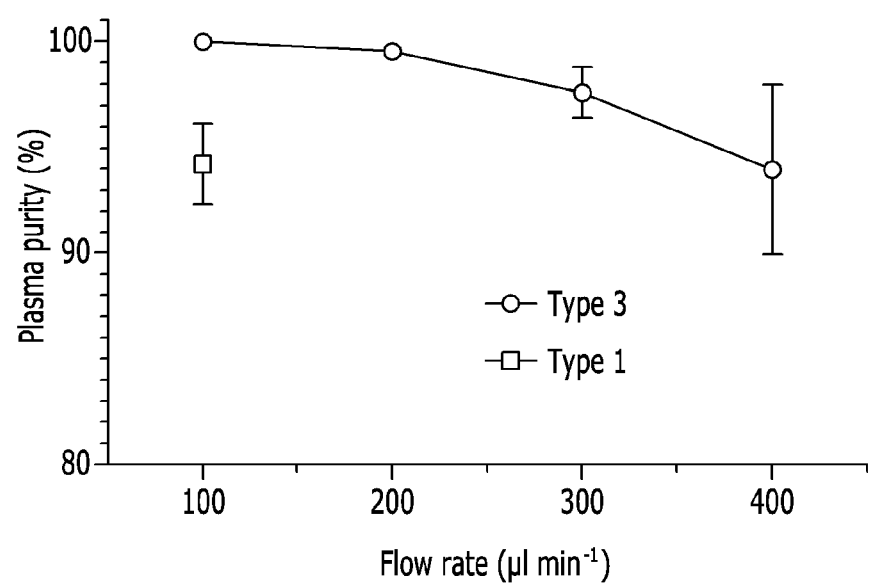
FIG. 7 is a graph illustrating the purity of blood plasma separated from the type 3 device for blood plasma separation according to the flow rate (n=3).

FIG. 7 shows a graph of the purity of blood plasma separated by the chip arrays of type 1 and type 3, according to the flow amount. FIG. 7 also shows that the chip array of type 3 has superior purity of separated blood plasma to that of the chip array of type 1.

Figure 8:
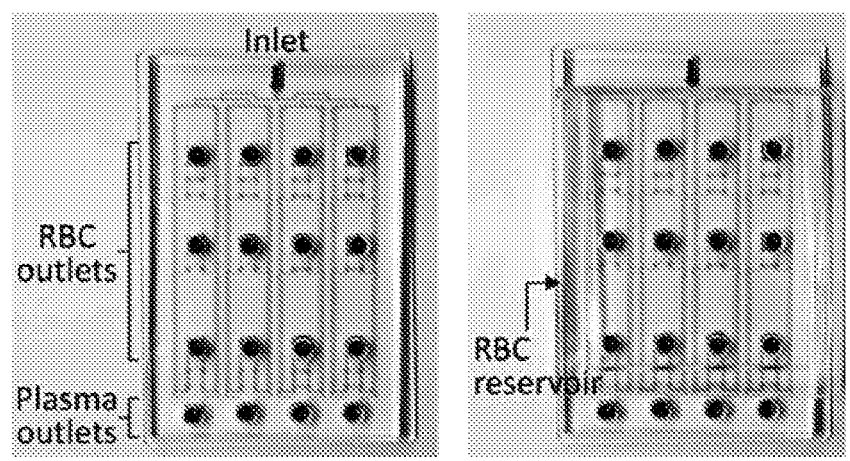
FIG. 8 is an illustrative image of a device for high throughput separation of blood plasma, in which RBCs discharged from each chip array are stored in a common repository.
Figure 9:
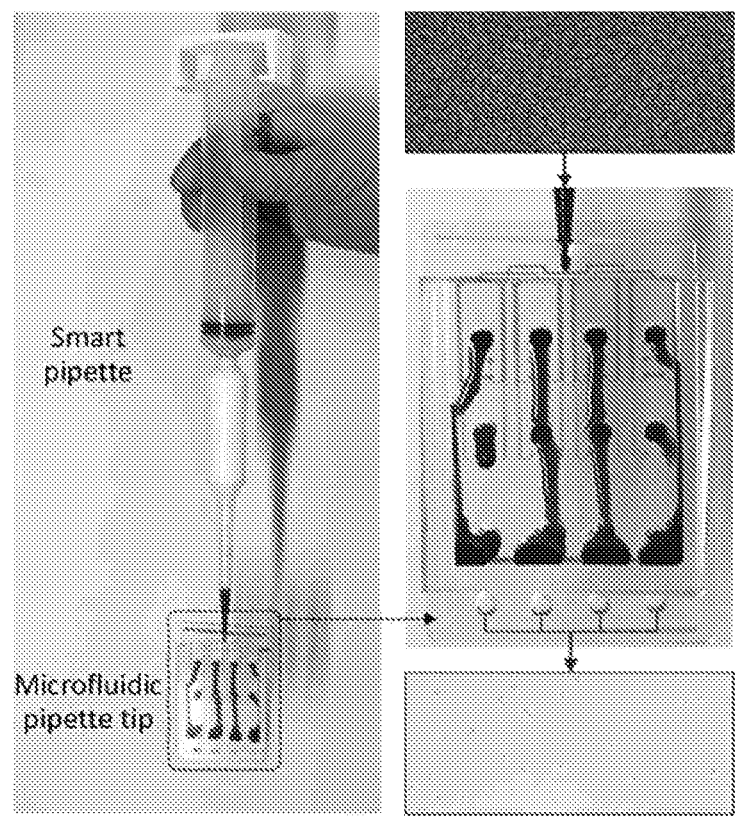
FIG. 9 is an illustrative image showing the operation of a device for blood plasma separation (including 8 chip arrays) while being connected to a syringe pipette (flow rate: 904.3±15.6 μL/min; extraction speed (blood volume separated according to time (min.)) purity of blood plasma separation at 51±1 μL/min: 99.88±0.01% (n=3)).

FIGS. 8 and 9 show that the amount of separated blood plasma can be increased by including the chip array in parallel. That is, it was confirmed that one chip array (type 3; including three chips (1 CSA+2 DSAs)) can treat approximately 100 μL/min, while the device for blood plasma separation (see FIG. 8) where eight chip arrays are included in parallel can treat 904.3±15.6 μL of blood per minute (see FIG. 9).

From the above description, it will be understood by those skilled in the art that the present invention may be embodied in other specific forms without departing from the spirit or essential characteristics thereof. In this regard, it should be understood that the above-described exemplary embodiments are to be considered in all respects only as illustrative and not restrictive. The scope of the present invention should be construed to cover all modifications and variations derived from the meaning and range of the claims and equivalents thereof as described below rather than the detailed description.

EXPLANATION OF REFERENCE NUMERALS

100: surfaces forming protrusions and depressions and surfaces at both sides
101: body part
102: continuous ridge
103: channel part
104: structure that cuts off the inner space of ridge
105: discrete ridge
200: substrate on the opposite surface of an uneven surface of body part
301: blood inlet
401: outlet for discharging blood cells
501: outlet for discharging blood plasma

The invention claimed is:

1. A chip for blood plasma separation, which comprises:
(i) a body part, in which a space through which blood can flow is integrally formed and a channel part and a ridge are alternately and continuously formed;
(ii) an inflow part, which is disposed at an upper region of the body part into which the blood inflows;
(iii) an outlet for discharging blood cells, which is located at one side surface of the body part; and
(iv) an outlet for discharging blood plasma, which is located at the other side surface of the body part,
wherein the ridge and the channel part communicate with each other in the space through which blood can flow,
the ridge forms a ridge space to communicate with the channel part, comprises an inner space having a height of a sum of the height of the channel part and the height of the ridge space, and is formed at an oblique angle of more than 0° and less than 90° with one side surface of the body part,
the ridge, which is inclined, is formed discretely by at least one structure that cuts off the inner space in an oblique angle of more than 45° and less than 90° with one side surface of the body part,
the one side surface where the outlet for discharging blood cells is located is a side surface having an angle of less than 90° with the inclined surface of the ridge, a lower surface connected with the side surface, or an edge region where the side surface is connected with the lower surface, and
the other side surface where the outlet for discharging blood plasma is located is the side opposite to the one side surface where the outlet for discharging blood cells is located, a lower surface connected with the side surface, or an edge region where the side surface is connected with the lower surface,
wherein the at least one structure is substantially perpendicular to the direction of flow.

2. The chip of claim 1, wherein the height ($h_r$) of the ridge space formed in the ridge is 1 μm to 20 μm, or the width of the ridge space formed in the ridge is 0.5 times to 3 times the height of the ridge space.

3. The chip of claim 1, wherein the length in the oblique direction of the ridge of the ridge space formed in the ridge is 2 times to 20 times the diameter of the red blood cells.

4. The chip of claim 1, wherein the height of the channel part is 2 um to 20 μm.

5. A method for blood plasma separation, comprising:
infusing blood into the fluidic chip for blood plasma separation of claim 1; and
collecting the blood plasma being discharged from the chip for blood plasma separation.

6. The method of claim 5, wherein the blood to be infused is whole blood, or blood prepared by a 1- to 20-fold dilution of the whole blood based on volume.

7. A chip array for blood plasma separation, comprising:
(1) a blood inlet into which blood is infused;
(2) a first part for blood plasma separation connected with the blood inlet (1);
(3) a second part for blood plasma separation connected with the first part for blood plasma separation; and
(4) a part for discharging blood plasma, wherein the first part for blood plasma separation is connected so that the blood infused into the blood inlet inflows, and comprises at least one chip for blood plasma separation comprising a continuous ridge, comprising: (i-1) a body part, in which a space through which blood can flow is integrally formed and the channel part and a ridge are alternately and continuously formed; (ii-1) an inflow part, which is disposed at an upper region of the body part into which the blood inflows; (iii-1) an outlet for discharging blood cells located at one side surface of the body part; and (iv-1) an outlet for discharging blood plasma located at the other side surface of the body part, wherein the ridge and the channel part communicate with each other in a space where the blood can flow, the ridge forms a ridge space to communicate with the channel part, comprises an inner space having a height of the sum of the height of the channel part and the height of the ridge space, and is formed at an oblique angle of more than 0° and less than 90° with one side surface of the body part, the inclined ridge is formed continuously in an oblique direction, the one side surface where the outlet for discharging blood cells is located is a side surface having an angle of less than 90° with the inclined surface toward the direction of blood flow of the ridge, a lower surface connected with the side surface, or an edge region where the side surface is connected with the lower surface, and the other side surface where the outlet for discharging blood plasma is located is the opposite side of the one side surface where the outlet for discharging blood cells is located, a lower surface connected with the side surface, or an edge region where the side surface is connected with the lower surface, and the second part for blood plasma separation is connected so that the blood plasma discharged from the part for discharging blood plasma of the ridge comprised in the first part for blood plasma separation inflows, and comprises at least one fluidic chip for blood plasma separation according to claim 1.

8. The chip array of claim 7, wherein the first part for blood plasma separation comprises at least one fluidic chip for blood plasma separation comprising the continuous ridge, and the second part for blood plasma separation comprises at least two chips for blood plasma separation comprising the discrete ridges.

9. A method for blood plasma separation, comprising:
infusing blood into the chip array for blood plasma separation of claim 7; and
collecting the blood plasma being discharged from the device for blood plasma separation.

10. The method of claim 9, wherein the blood to be infused is whole blood, or blood prepared by a 1- to 20-fold dilution of the whole blood based on volume.

11. A kit for blood plasma separation, comprising:
a chip array for blood plasma separation of claim 8; and
a part for supplying blood connected with a blood inlet of the chip array for blood separation.

12. A device for blood plasma separation comprising at least one chip array for blood plasma separation of claim 7.

13. The device of claim 12, wherein the first part for blood plasma separation comprises at least one fluidic chip for blood plasma separation comprising the continuous ridge, and the second part for blood plasma separation comprises at least two chips for blood plasma separation comprising the discrete ridges, which are comprised in each chip array for blood plasma separation.

14. A method for blood plasma separation, comprising:
infusing blood into the device for blood plasma separation of claim 13; and
collecting the blood plasma being discharged from the device for blood plasma separation.

15. The method of claim 14, wherein the blood to be infused is whole blood, or blood prepared by a 1- to 20-fold dilution of the whole blood based on volume.

16. A method for blood plasma separation, comprising:
infusing blood into the device for blood plasma separation of claim 10; and
collecting the blood plasma being discharged from the device for blood plasma separation.

17. The method of claim 16, wherein the blood to be infused is whole blood, or blood prepared by a 1- to 20-fold dilution of the whole blood based on volume.

18. A kit for blood plasma separation, comprising:
the device for blood separation of claim 12; and
a part for supplying blood connected with a blood inlet of the device for blood separation.

* * * * *